United States Patent [19]

Quinn et al.

[11] 4,019,707
[45] Apr. 26, 1977

[54] DEVICE FOR SUPPORTING FLUID RECEPTACLES

[75] Inventors: David G. Quinn, Round Lake, Ill.; Richard A. Rauschenberger, Brookfield, Wis.

[73] Assignee: Will Ross, Inc., Milwaukee, Wis.

[22] Filed: Oct. 30, 1975

[21] Appl. No.: 627,442

[52] U.S. Cl. .............................. 248/95; 128/275; 248/228

[51] Int. Cl.² ........................................ B65B 67/12

[58] Field of Search ............. 248/95, 102, 214, 215, 248/228, 231, 340; 128/275; 224/4 C, 5 R

[56] References Cited

UNITED STATES PATENTS

| | | | |
|---|---|---|---|
| 3,312,221 | 4/1967 | Overment | 248/95 X |
| 3,371,897 | 3/1968 | Serany et al. | 248/95 |
| 3,534,738 | 10/1964 | Huck | 248/95 X |
| 3,612,459 | 10/1971 | Walls | 248/340 X |
| 3,893,647 | 7/1975 | Kennedy | 248/231 |

*Primary Examiner*—William H. Schultz
*Attorney, Agent, or Firm*—John A. Dhuey

[57] ABSTRACT

A device is described for attaching fluid collection bags on frame type members such as used in hospital beds. The device, supported on the top of the frame member, hangs down so as to present a convenient attachment point for fluid collection bags, and is releasably secured to the frame member. Use of a unique two-stage locking mechanism and a semi-rigid, resilient wing permits attachment to variously sized frame members.

15 Claims, 5 Drawing Figures

DEVICE FOR SUPPORTING FLUID RECEPTACLES

This invention is concerned with a device which functions as a adapter to secure containers, which normally are difficult to retain in fixed positions, to frame-like members. In particular, it is concerned with a device for attaching fluid collection bags, such as urinary collection bags, to frame members of a hospital bed.

Commonly, fluid collection receptacles such as urinary drainage bags are provided with an open-ended hook so that they may be hung near a patient during the course of fluid collection. It has heretofore been a problem to conveniently place such collection receptacles near the patient and yet at a place where they will not be struck and possibly spilled by hospital personnel going about their normal duties. Often collection receptacles have been hung on stands for that purpose placed near the bed of the patient. However, such stands are prone to tipping and must be circumvented by hospital personnel when carrying out their duties about the bed of a patient.

There has been discovered a particularly convenient, low-cost device which can be used as a adapter to securely attach a fluid receptacle to the bed frame supporting a patient. The instant device avoids the above-discussed problems to provide a secure attachment for a fluid collection receptacle while not interfering with the normal movements of hospital personnel. Since the collection receptacle is attached on the bed, the entire area around the bed is free for necessary activity.

The invention will be described with reference to the following drawings in which.

Figure 1:
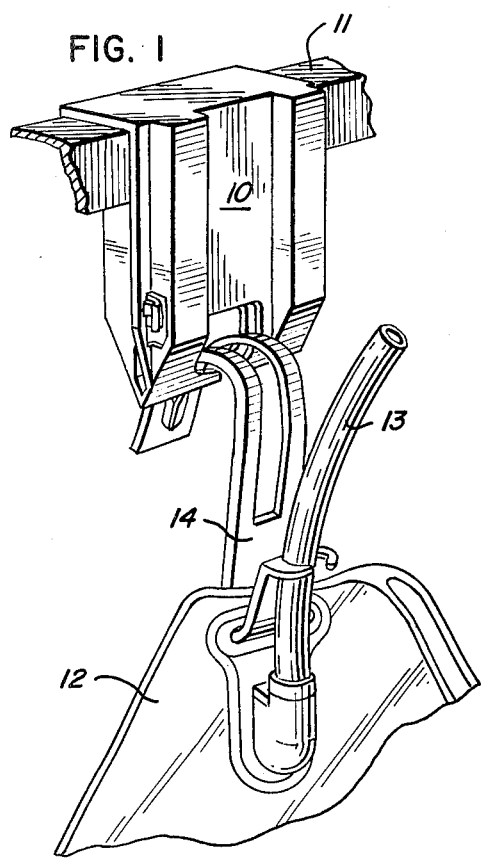
FIG. 1 is a perspective view of the device of this invention, as it is typically to be used.
Figure 2:
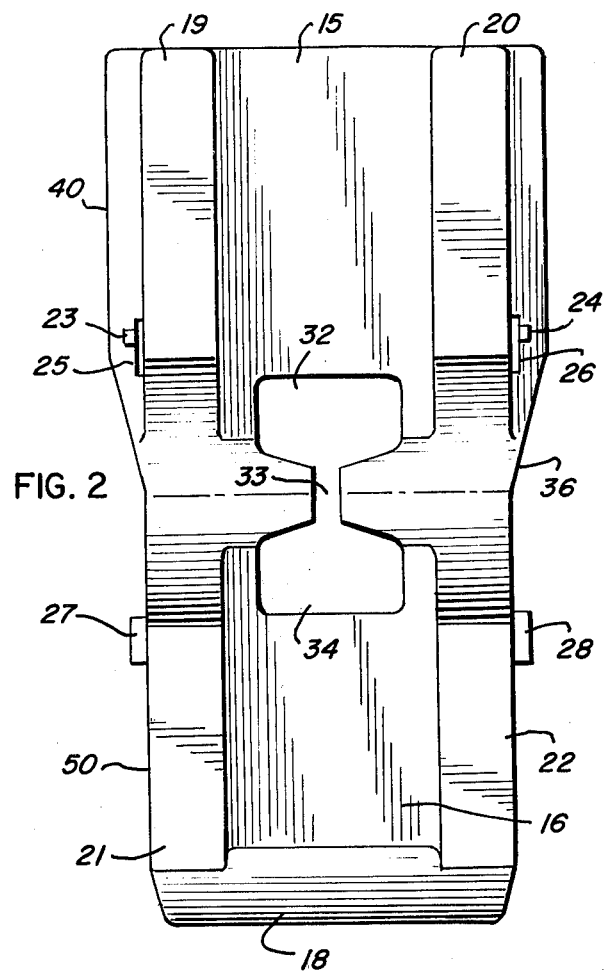
FIG. 2 is a plan view of the device of this invention.

With reference to the drawings the device 10 of this invention is utilized by securing it to a frame member 11 and hanging from it a fluid receptacle 12, having a tube 13 to receive fluid from a patient, by a hook 14 attached to receptacle 12.

Device 10 preferably is formed as a unitary device, as, for example, by conventional plastic molding techniques. Device 10 comprises a first member 40 having a substantially-flat main portion 15 and a substantially-flat minor portion 17 perpendicularly attached to one end of said main portion 15, and a second member 50 having a substantially-flat main portion 16 and a semi-rigid wing 18. Perpendicular portion 17 is adapted to overlay the top of a frame member 11 to provide the necessary support for device 10. Member 50 operates in cooperation with member 40 as a retention means to firmly hold device 10 on a frame member 11 when device 10 is in its closed position.

Figure 3:
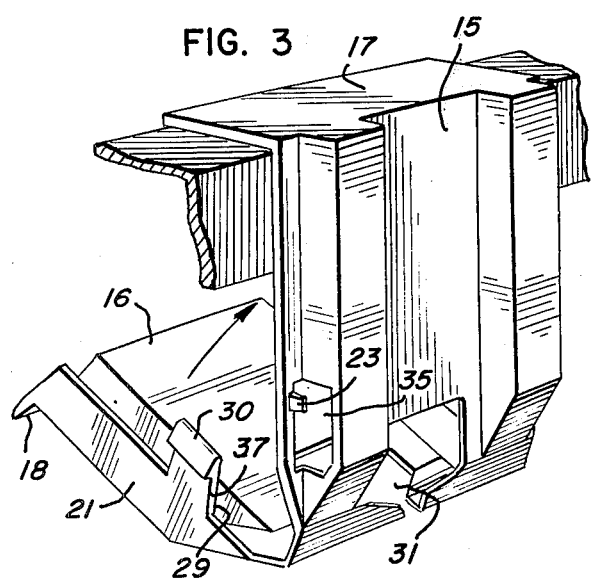
FIG. 3 is a perspective view of the preferred embodiment of the invention in its open configuration.
Figures 4, 5:
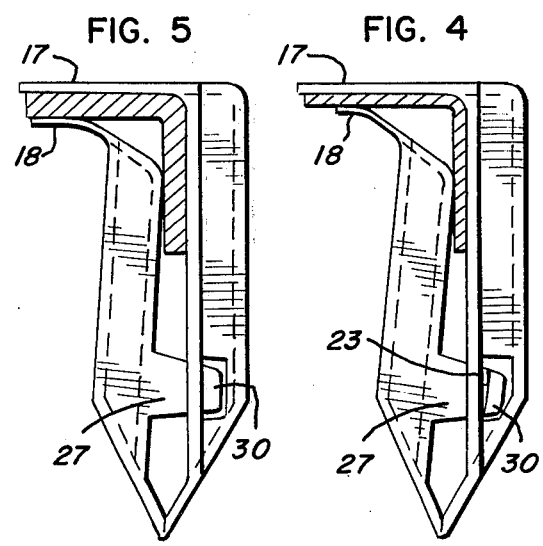
FIG. 4 is a side view of the preferred embodiment of the invention in its closed configuration.
FIG. 5 is a side view of another embodiment of the invention it its closed configuration.

Members 40 and 50 are hingedly-joined at juncture 36. Conventional hinging means can be used. However, since device 10 usually is molded, it is preferable to form juncture 36 by reducing the thickness of members 40 and 50 near their line of joining. Members 40 and 50 then may rotate about said juncture 36 from an open position, such as shown on FIG. 3, to a closed position, such as shown in FIGS. 4 and 5.

Member 40 conveniently is molded with rectangular channels 19 and 20 formed therein. Those channels increase the rigidity of device 10 and provide a convenient location for the latching means which will be described hereinbelow. Similarily, member 50 is molded with rectangular channels 21 and 22 formed therein to provide added rigidity to member 50.

The preferred latching mechanism to retain members 40 and 50 in a closed position, and subsequently secure a frame member 11 therebetween, comprises outwardly extending nubs 23 and 24, located on the outside surface of said main portion 15 near apertures 25 and 26, formed in main portion 15 and adjacent the sides of rectangular channels 19 and 20 which face the lateral edge of member 40. Apertures 35 are formed in the sides of channels 19 and 20 and are coextensive with apertures 25 and 26. Nubs 23 and 24 are not immediately adjacent the respective edge of apertures 25 and 26 at the point where the nubs are joined to main portion 15 of member 40. Consequently, a ledge is provided adjacent aperture 25 and 26 so that the cooperating latching means on member 50 can engage member 15 or nubs 23 and 24 and hold device 10 in either a first or second closed position. The particular closure position will depend on the size of the frame member to which device 10 is being attached.

The latching means formed on member 50 conveniently consists of appendages 27 and 28, formed with a flexible neck portion 29 attached to the outer edge of each rectangular channel and a rigid, wedge-shaped head portion 30. Head 30, at its juncture with neck 29, is thicker than neck 29. The resultant free surface 37 thus is capable of contacting the outer surface of main portion 15 when members 40 and 50 are placed in a first closed position. Surface 37 effectively locks members 40 and 50 in a closed position until flexible neck portion 29 is forced inwardly to free surface 37 from main portion 15 and release members 40 and 50. The sizes of head 30 and aperture 35 are chosen appropriately so that head 30 can pass therethrough. In the second closed position, surface 37 rests upon nub 23, as is best seen in FIG. 4 In that manner, it is possible for device 10 to be used on frame members having different dimensions.

Also, semi-rigid wing 18, extending outwardly from main portion 16, automatically adjusts to variously sized frame members. The cooperation of semi-rigid wing 18 and the two-stage closure permit device 10 to be secured to frame members with a minimum of free-play.

A fluid receptacle can be attached to device 10 by means of a hook placed through opening 31. Typically, opening 31 is formed from holes 32 and 34, in members 40 and 50, respectively, connected by a passage 33. Although such an embodiment is preferred, it is apparent that passage 33 could be omitted from the device without impairing its effectiveness. Elimination of passage 33 would be necessary where fluid receptacles are provided with narrow support hooks which might slip through passage 33. Additionally, other attachment means could be placed on member 40 for engaging a fluid receptacle.

In use, device 10 is placed with top portion 17 resting on the top of a frame member 11. Then member 50 is rotated upwardly toward member 40 until latching means 27 and 28 are secured on member 40. Because of the wedge-shape of head 30, the appendages 27 and 28 are guided into apertures 25 and 26 by the inclined face of head 30. Wing 18 contacts the underside of the frame member to form a secure attachment.

The invention has been described with respect to the drawings for purposes of illustration only. They are not meant to limit the invention since changes will be apparent to those skilled in the art without departing from the spirit or scope of this invention.

What is claimed is:

1. A device for supporting fluid receptacles on frame members comprising:
   a first member having a substantially-flat main portion and a substantially-flat minor portion perpendicular to said main portion at one end thereof for support on the top of a frame member;
   attachment means on said main portion for engaging a fluid receptacle;
   a second member having a substantially-flat main portion hingedly-joined at one end to said first member at the end opposite said perpendicular portion for rotation from an open position to a closed position, and having a semi-rigid, wing at the other end thereof for contacting the lower surface of a frame member, said wing extending outwardly and upwardly below said perpendicular portion when said device is in its closed position; and
   latching means on said main portions of said first and second members for cooperative engagement thereof and operable to secure a frame member between first and second members.

2. A device as in claim 1 wherein said attachment means is an opening in said first and second members proximate the hinged portions and adapted to retain a fluid receptacle therein.

3. A device as in claim 2 wherein said opening comprises a hole in each of said first and second members connected by a passage through the hinged portion thereof.

4. A device as in claim 1 wherein said first and second members are integrally-formed and hingedly-joined by a portion of said first and second members having a reduced thickness.

5. A device as in claim 4 wherein said attachment means comprises an opening formed as a hole in each of said first and second members connected by a passage through the hinged portion thereof.

6. A device as in claim 1 wherein said latching means comprises an aperture in said main portion of said first member and retention means on said main portion of said second member for engagement with said first member and retention in said aperture when said first and second members are in the closed position.

7. A device as in claim 6 wherein said retention means releasably engages said first member.

8. A device as in claim 7 wherein said retention means is an appendage on the main portion of said second member having a flexible neck portion and a rigid wedge-shaped head for retention in said aperture and engagement with said first member.

9. A device as in claim 1 wherein said latching means is operable to latch in at least two positions.

10. A device as in claim 9 wherein said latching means comprises an aperture in said main portion of said first member, an outwardly extending nub proximate the edge of said aperture, and retention means on said main portion of said second member operable to engage said first member at a first position and engage said nub at a second position.

11. A device as in claim 10 wherein said retention means comprises an appendage attached to said main portion of said second member, said appendage having a flexible neck portion and a rigid wedge-shaped head adapted to engage said first member at said first position and said nub at said second position.

12. A device for supporting a fluid receptacle on a frame comprising:
    a first member having a substantially-flat main portion and a substantially-flat minor portion perpendicular to said main portion at one end thereof for support on the top of a frame member, said main portion having a rectangular channel formed therein near each outer lateral edge thereof and substantially coextensive with the length of said main portion, said main portion further having an opening therethrough between said channels and near the bottom edge of said main portion for attachment of a fluid receptacle;
    a second member having a substantially-flat main portion hingedly-joined to the end of said first member opposite said perpendicular portion for rotation between an open position and a closed position, and having a semi-rigid, outwardly-extending wing at the other end thereof for contacting the lower surface of a frame member; and
    latching means comprising a first aperture in the side of said rectangular channel proximate the lateral edge of said first member and a second aperture in said main portion of said first member, said second aperture being coextensive with said first aperture and connecting therewith, and an appendage on the main portion of said second member having a flexible neck portion and a rigid, wedge-shaped head portion adapted for retention in said first and second apertures and engagement with said first member.

13. A device as in claim 12, wherein said latching means further comprises a outwardly-extending nub intermediate the edge of said second aperture and the lateral edge of said first member, whereby said wedge-shaped head can alternatively engage said first member or said nub for closure of said first and second members at two positions.

14. A device as in claim 12 wherein said second member has a rectangular channel formed therein at the outer lateral edge thereof and substantially coextensive with the length of the main portion of said second member.

15. A device as in claim 14 wherein said appendage is integrally joined to the outer edge of said channel.

* * * * *